United States Patent [19]

Warriner

[11] Patent Number: Plant 6,318

[45] Date of Patent: Oct. 4, 1988

[54] ROSE PLANT JACHYP

[75] Inventor: William A. Warriner, Tustin, Calif.

[73] Assignee: Jackson & Perkins Company, Medford, Oreg.

[21] Appl. No.: 936,009

[22] Filed: Nov. 28, 1986

[51] Int. Cl.[4] ..... A01H 5/00

[52] U.S. Cl. ..... Plt./18

[58] Field of Search ..... Plt./18

*Primary Examiner*—James R. Feyrer

*Attorney, Agent, or Firm*—Majestic, Gallagher, Parsons & Siebert

[57] ABSTRACT

A hybrid tea rose variety having bright pink exhibition-style blooms, dark green leathery foliage, pleasant flower fragrance, long flower stem and vigorous, upright growth habit.

1 Drawing Sheet

This present invention relates to a new and distinct variety of rose plant of the hybrid tea class which was originated by crossing the variety Honor, U.S. Plant Pat. No. 4,167, with the variety American Dawn, U.S. Plant Pat. No. 3,666.

The primary objective of this breeding was to produce a new rose variety of the hybrid tea class with large pink flowers and dark green foliage. This objective was substantially achieved along with other desirable improvements as evidenced by the following unique combination of characteristics which are outstanding in the new variety and which distinguish it from its parents as well as from all other varieties of which I am aware:

1. Long exhibition-style bud and bloom;
2. Bright pink flower color;
3. Long flowering stems and peduncle;
4. Vigorous upright growth habit;
5. Pleasant fragrance; and
6. Dark green leathery foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Honor, U.S. Plant Pat. No. 4,167.

*Pollen parent.*—American Dawn, U.S. Plant Pat. No. 3,666.

Classification:

*Botanical.*—Rosa hybrid.

*Commercial.*—Hybrid tea.

FLOWER

Observations made from specimens grown in a greenhouse at Irvine, Calif.

Blooming habit: Continuous.

Bud:

*Size.*—1½" to 2" when petals start to unfurl.

*Form.*—Long, pointed ovoid.

*Color.*—When sepals first divide, Red Group 52B to C; when half blown, upper side of petals Red Group 52C; lower side of petals Red Group 52C.

*Sepals.*—Color: Green Group 138A. Three appendaged sepals normally to occasionally heavily appendaged. Two unappendaged sepals hairy edged.

*Receptacle.*—Color: Green Group 138A. Shape: Funnel. Size: Large. Surface: Smooth.

*Peduncle.*—Length: Long. Surface: Smooth, glandular. Color: Bronzy, Strength: Stiff, erect.

Open bloom:

*Size.*—Large. Average open size 5".

*Borne.*—Singly.

*Stems.*—Long, strong.

*Form.*—When first open, high center. Permanence: Retains its form to the end, outer petal edges slightly curled.

*Petalage.*—Number of petals under normal conditions: 30-35.

*Color.*—Center of flower: Upper side of petals, Red Group 52B; reverse side of petals, Red Group 52B. Base of petals, small yellow half circle at base of attachment. Major color: Red Group 52B.

*Variegations.*—None.

*Discoloration.*—General tonality at end of first day: None. Third day: If very sunny and hot weather, there can be a general fading to Red Group 52D.

*Fragrance.*—Moderate.

Petals:

*Texture.*—Medium.

*Shape.*—Round.

*Form.*—Tips slightly recurved.

*Arrangement.*—Imbricated.

*Persistence.*—Drop off cleanly.

Lastingness.—On the plant, long. As cut flower, long.

Reproductive parts:

*Anthers.*—Large. Color: Yellow. Arrangement: Regular around styles.

*Filaments.*—Color: Greenish.

*Pollen.*—Lemon yellow.

*Styles.*—Color: White.

*Stigmas.*—Color: Red. During cool nights, the stigma and style may become vegetative.

PLANT

Form: Bush.
Growth: Very vigorous.
Foliage: Number of leaflets on normal mid-stem leaves: 5.
*Size.*—Medium.
*Quantity.*—Normal.
*Color.*—New foliage: Red. Old foliage: Dark green.
Leaflets:
*Shape.*—Oval.
*Texture.*—Leathery.
*Edge.*—Serrated.
*Serration.*—Single.
*Petiole.*—Rachis: Color: Reddish. Underside: Smooth with a few prickles.
*Stipules.*—Bearded.
*Disease resistance.*—Susceptible to mildew, under normal growing conditions at Irvine, Calif.

Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Hooked downward.
*Color when young.*—Red.
Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of its bright pink exhibition-style blooms, dark green leathery foliage, pleasant flower fragrance, long flower stem and vigorous, upright growth habit.

* * * * *

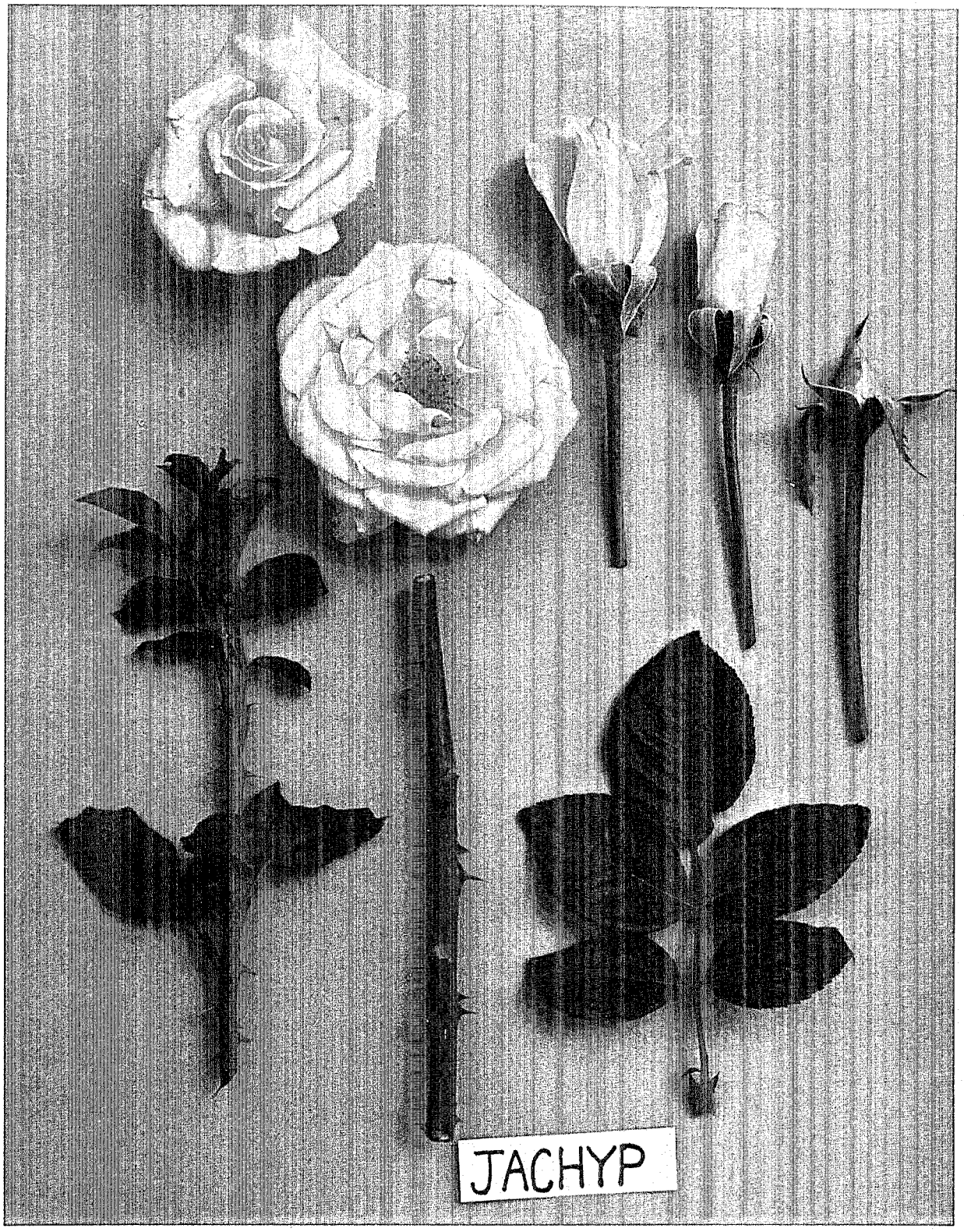
JACHYP